(12) United States Patent
Tamura (10) Patent No.: US 6,425,868 B1
(45) Date of Patent: Jul. 30, 2002

(54) ULTRASONIC IMAGING SYSTEM

(75) Inventor: Tadashi Tamura, North Haven, CT (US)

(73) Assignee: Aloka Co., Ltd. (JP)

(*) Notice: Subject to any disclaimer, the term of this patent is extended or adjusted under 35 U.S.C. 154(b) by 0 days.

(21) Appl. No.: 09/360,658

(22) Filed: Jul. 26, 1999

(51) Int. Cl.[7] ............................................. A61B 08/00
(52) U.S. Cl. ..................................... 600/454; 600/465
(58) Field of Search ............................... 600/443, 447, 600/454, 455, 456

(56) References Cited

U.S. PATENT DOCUMENTS

| | | | |
|---|---|---|---|
| 4,573,477 A | | 3/1986 | Namekawa et al. |
| 4,622,977 A | | 11/1986 | Namekawa et al. |
| 4,641,668 A | | 2/1987 | Namekawa |
| 4,651,742 A | | 3/1987 | Namekawa et al. |
| 4,651,745 A | | 3/1987 | Namekawa et al. |
| 5,501,223 A | * | 3/1996 | Washburn et al. .......... 600/455 |
| 5,980,458 A | * | 11/1999 | Clark ......................... 600/437 |
| 6,056,691 A | * | 5/2000 | Urbano et al. .............. 600/443 |
| 6,102,864 A | * | 8/2000 | Hatfiled et al. ............. 600/454 |

OTHER PUBLICATIONS

O. Bonnefous and P. Pesque "Time Domain Formulation Of Pulse–Doppler Ultras0und And Blood Velocity Estimation By Cross Correlation" pp. 73–85, Academic Press, Inc., 1986.

Chihiro Kasai, Koroku Namekawa, Akira Koyano and Ryozo Omoto "Real Time Two Dimensional Blood Flow Imaging Using an Autocorrelation Technique" pp. 458–464, IEEE Transactions on Sonics and Ultrasonics, May, 1985.

M. Kaveh, IR.K. Mueller, J.F. Greenleat "Real–Time Two–Dimensional Doppler Flor Mapping Using Auto–Correlation" Acoustical Imaging, vol. 13, 1984.

* cited by examiner

Primary Examiner—Marvin M. Lateef
Assistant Examiner—Maulin Patel
(74) Attorney, Agent, or Firm—Cantor Colburn LLP (57) ABSTRACT

An ultrasound imaging system provides for high density scanning (transmit/receive) of color flow signals. The ultrasound scan sequence of each transmitted and received color flow ultrasound beam is laterally spaced through the imaging field to calculate flow velocities. The color flow beams are transmitted and received only once at each position along the horizontal scanning axis of the imaging field. The scanning technique of the present invention enables a large number of color flow lines to be acquired while keeping a high frame rate. The color line density is comparable to that of a B-mode image. A method of high-speed calculation or a high-speed autocorrelation is also provided to process the greater number of signals generated by the present scanning technique. A time-sharing scanning technique between color flow and B-mode images is also provided to synchronize blood flow and tissue (B-mode) images together.

36 Claims, 9 Drawing Sheets

ULTRASONIC IMAGING SYSTEM

FIELD OF THE INVENTION

The present invention relates to the field of ultrasonic imaging as used for example in medical diagnostic scanning. More particularly, the invention relates to an improved ultrasonic imaging system that is capable of accurately displaying the velocity distribution of movement of blood flow within a living organism.

BACKGROUND OF INVENTION

Ultrasound imaging systems for medical diagnostics scan a subject with ultrasound beams in a field of sector or rectangular pattern and provide a two-dimensional display of the scanned field. The imaging system includes a transducer that emits and focuses the ultrasound beams along certain linear directions or scan lines. The emitted beams reflect back, in the form of an echo of acoustic scattering to the transducer along the same scan lines. Subsequently, the received beams are converted to electrical signals, which are then processed to generate an image on a two-dimensional display representative of a planar cross-section through the subject. The resolution of the images depends on how well the beams are locally focused along the scan lines, as well as the number of scan lines per sector scanned.

Modern ultrasound imaging systems may scan a subject to provide a tissue image (or B-mode image) and a blood flow image (or color flow image) of the scanned sector field. Generally, B-mode imaging produces a two-dimensional gray scale image of the tissue of the subject. The imaging system generates a single frame of a B-mode image by scanning multiple beams in a given sector or rectangular pattern. The ultrasound imaging systems sequentially emit and receive a plurality of beams (or transmissions) through the subject. Specifically, the beams are swept through the sector at small lateral increments to generate one frame of a B-mode image. Each frame includes as many as 60 to 400 laterally spaced beams.

In addition, color flow imaging has been developed to display blood flow as a two-dimensional color image. A B-mode image and a color flow image are superimposed to provide a composite image of the blood flow through the tissue or organ of the subject being scanned. The principle of detecting blood flow may be either the Doppler technique or a time-shift technique. For the Doppler technique, an autocorrelation technique has been implemented in most commercial ultrasound systems. This autocorrelation technique in principle can obtain a velocity or a phase shift between two consecutive complex Doppler signals by calculating the complex product between the two after wall filtering. However, in reality, averaging of several pairs is necessary to enhance blood flow sensitivity by increasing signal to noise ratio in the signal from the human body.

Figure 1:
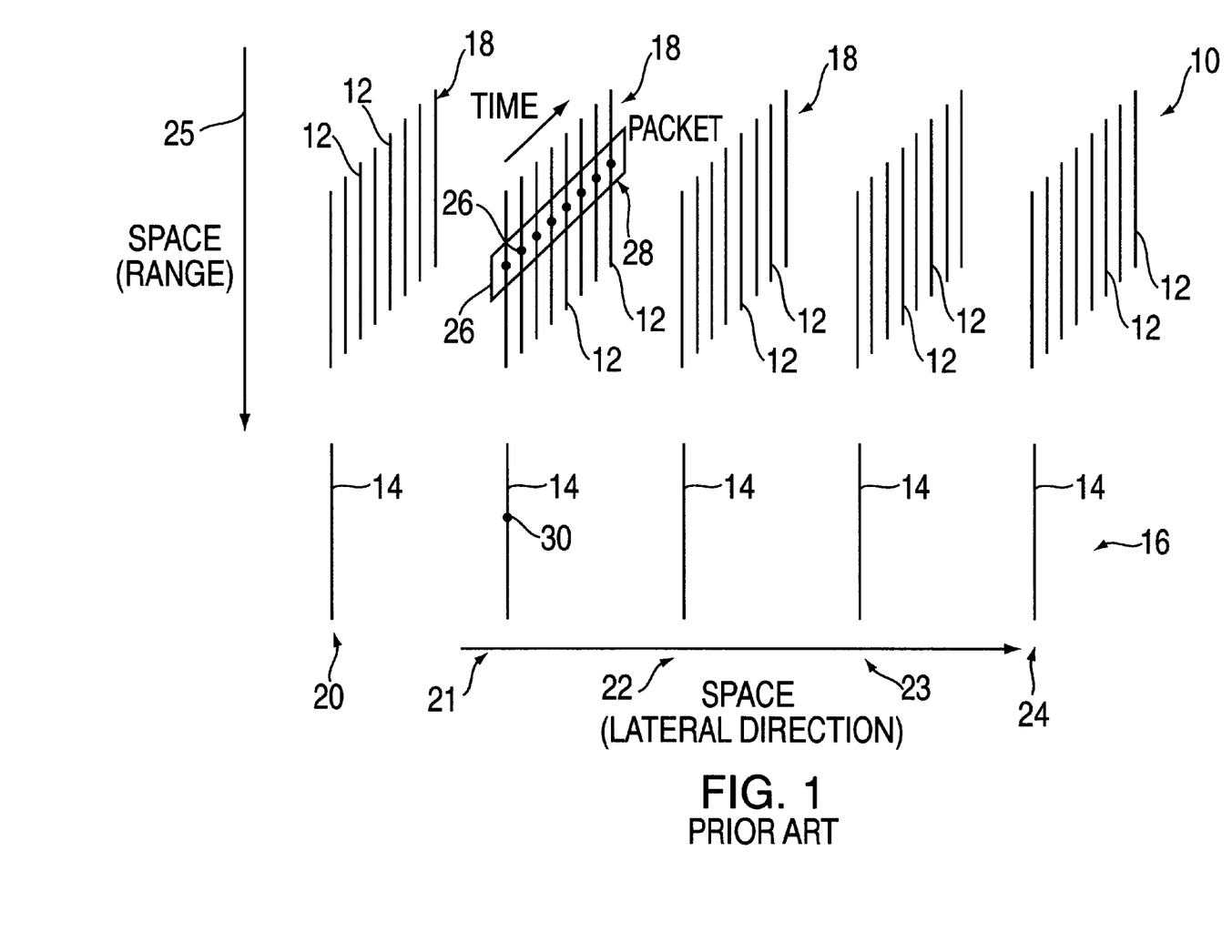
FIG. 1 is a graphical representation of a prior art method of scanning color flow beams.

The prior art technique of color flow imaging is diagrammatically shown in FIG. 1. The upper panel 10 illustrates multiple transmit/receive ultrasound beams 12 that create a color flow image output line 14, shown in the lower panel 16. The prior art ultrasound system transmits and receives a plurality of packets or groups 18 of ultrasound beams 12 at spaced lateral positions 20–24 along the imaging field of the subject being scanned. Each packet 18 comprises approximately between 6–16 ultrasound beams. The packets of beams are transmitted at an interval, or pulse repetition time (PRT) at each position. For instance, as a single frame of the imaging field is scanned, the ultrasound imagine(, system transmits and receives a first packet of ultrasound beams (8 beams) at a first position 20. The second packet of beams are scanned at a second position 21 laterally-spaced from the first position. Further packets 18 of beams 12 are emitted and received in the lateral direction until the entire field is scanned. Five (5) lateral positions 20–24 are illustrated to depict a sample of packets 18 of beams for scamming the field.

As a result, five (5) color flow output lines 14 are calculated and displayed in the lower panel 16 for each respective packet 18 of ultrasound beams 12. Each beam 12 is representative of received and complex Doppler signals of varying depth or range in the body. For example, solid circles 26 in the upper panel 10 depict a subpacket 28 of received and digitized signals representative of the body structure of a subject at a predetermined depth in the body or distance from the transducer. The solid circle 30 in the lower panel 16 shows a flow velocity output calculated from the subpacket 28 of the received and digitized signals (solid circles) 26 shown in the upper panel 10. One skilled in the art will recognize that each ultrasound beam comprises many (up to several hundred) received and digitized signals 26, and each color flow output line 14 comprises a corresponding number of calculated velocities 30, although not specifically shown in the FIG. 1.

In order to capture motions of tissues or blood flow at reasonably fast frame rate, the number of color flow output lines 14 is limited and far less than the number of B-mode beams. As shown hereinbefore, each color flow image output line 14 represents eight (8) transmitted color flow beams 12 and therefore, the B-mode image comprises approximately eight times as many received output signals as the color flow image for an equal number of scan B-mode and color flow scan lines for each frame. Consequently, the color flow output lines 14 density is much less than that of B-mode output beams, resulting in lower spatial resolution than that of B-mode images.

SUMMARY OF THE INVENTION

This invention offers advantages and alternatives over the prior art by providing an ultrasound imaging system that provides for high density scanning (transmit/receive) of color flow signals. The ultrasound scan sequence of each transmitted and received color flow ultrasound beam is laterally spaced through the imaging field to provide a high density of color flow lines. The scanning technique of the present invention enables a large number of color flow lines to be acquired while keeping a high frame rate. The color line density is comparable to that of B-mode images. A method of high-speed calculation, or a high-speed autocorrelation is also provided to process the greater number of signals generated by the present scanning technique and therefore, maintain a high frame rate. A time sharing scanning technique between color flow and B-mode images is also provided in order to more accurately synchronize blood flow and tissue (B-mode) images together. Furthermore, color flow beams may also used for B-mode imaging to thereby increase the frame rate.

In accordance with an embodiment of the present invention, a method for generating color flow images for an imaging system includes scanning sequentially a predetermined number of color flow beams through an imaging field wherein the color flow beams are laterally spaced through the imaging field. The color flow beams define a first packet of color flow beams. The first packet of color flow beams is processed to generate a first color flow output signal. An additional color flow beam, which is laterally spaced from a last color flow beam of the first packet, is scanned. The color flow beams of the first packet and the additional color flow beam, excluding a first color flow beam of the first packet, define a second packet. The second packet of color flow beams is processed to generate a second color flow output signal. This process continues for many color flow beams. A color flow image is generated from the first and second color flow signals as well as many other signals.

Preferably, the processing of the second packet of color flow beams includes using the results of the autocorrelation of complex signals representative of each color flow beam of the first packet at a predetermined depth. A complex product of a complex signal of the last color flow beam of the first packet and a complex signal of the additional color flow beam at the predetermined depth is determined as a new complex product. A complex product of a complex signal of the first color flow beam of the first packet and a complex signal of a second color flow beam of the first packet at the predetermined depth is determined as an old complex product. The autocorrelation, the new complex product and negative of the old complex product are summed to determine a complex signal or an autocorrelation representative of the color flow output signal in the second color output line at the predetermined depth.

In accordance with another embodiment of the present invention, a method for scanning color flow beams and B-mode beams of an imaging system for one frame of an imaging field includes scanning color flow beams through a first portion of the imaging field. B-mode beams are scanned through the first portion of the imaging field. Additional color flow beams are scanned through a second portion of the imaging field, which is adjacent to the first portion after scanning color flow beams and B-mode beams through the first portion of the imaging field. B-mode beams are scanned through the second portion of the imaging field after scanning color flow beams and B-mode beams through the first portion of the imaging field.

BRIEF DESCRIPTION OF DRAWINGS

Referring now to the drawings wherein like elements are numbered alike in the several FIGURES.

DETAILED DESCRIPTION OF THE INVENTION

Figure 2:
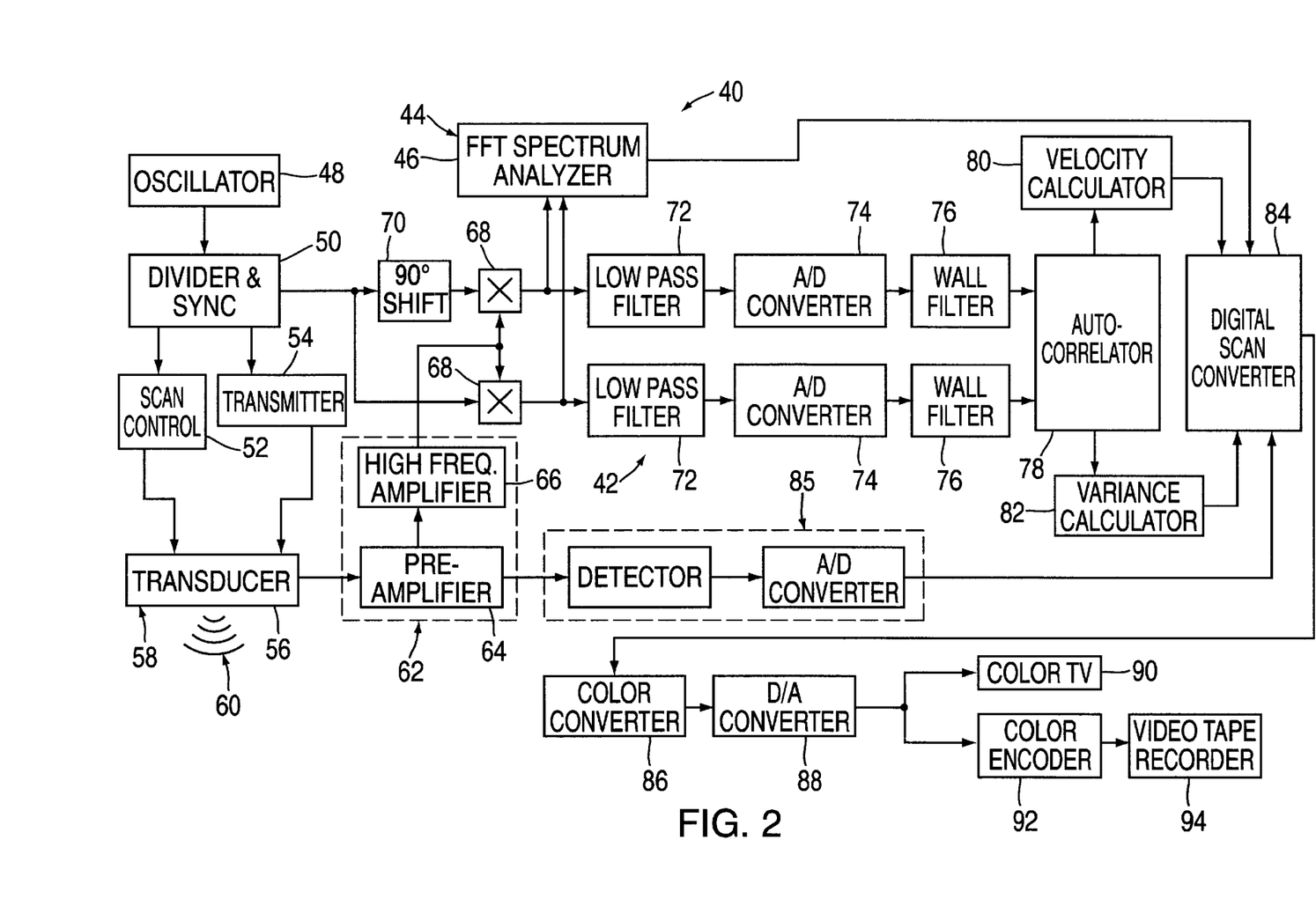
FIG. 2 shows a schematic representation of an ultrasound imaging system.

In FIG. 2, there is shown a block diagram of an ultrasound imaging system, generally designated 40, for generating two-dimensional color flow images of blood flow of a subject. The imaging system 40 includes both a conventional B-mode imaging unit, a color flow imaging unit 42 and a pulsed-Doppler unit 44 provided with a fast Fourier transform (FFT) spectrum analyzer 46. Images obtained by these units and color flow images are displayed simultaneously and superimposed.

A high-frequency oscillator 48 provides an output signal to a divider 50 that provides clock pulses to trigger various units and provide a continuous wave required for the demodulation of Doppler signals. A signal from a scan control unit 52 and transmitter 54 are provided to a transducer 56 of a probe 58, which in response to the signals emits acoustic waves or ultrasound beams 60 to the subject. The transducer then receives the beams back from the subject and provides a signal representative of the reflected wave. The transducer 56 comprises an array of a plurality of imaging elements (not shown). Each element is formed of a piezoelectric element that generates an acoustic signal in response to an electric signal or generates an electrical signal in response to an acoustic vibration.

Signals received through the transducer 56 are provided to a receiver 62, which first amplifies the received signal by a pre-amplifier 64 and a high-frequency amplifier 66. The amplified signal is then conveyed to a pair of quadrature detectors 68, where the phases of the mixing reference frequency differ by 90 degrees at 70. The output signals of the quadrature detectors 68 are filtered by low pass filters 72. Since the reference frequency is made identical to that of the transmitting acoustic wave, the outputs from the low-pass filters become the complex Doppler frequencies that have been shifted by Doppler effects, and the pair of outputs also become complex signals with phases that differ by 90 degrees. The pair of complex signals are converted to digital signals by analog-digital (A/D) converters 74 and then passed through wall filters 76 and an autocorrelator 78.

The wall filters 76 are low-frequency rejection filters that eliminate large echo signals from stationary or slowly moving tissues, which respectively have a zero or low Doppler frequency shift. The output of the autocorrelator 78 is conveyed to a velocity calculator 80 and a variance calculator 82 that respectively calculate the mean velocity value and the variance of Doppler signals. The outcome is then recorded in a digital scan converter (DSC) 84. The DSC additionally records the B-mode or M-mode images that have been obtained with conventional equipment 85 and FFT-analyzed spectra of the blood flow by the FFT spectrum analyzer 46.

A color converter 86 converts the data stored in the DSC 84 to chrominance signals. Firstly, with regard to the phase $\phi(T, t)$ that has been obtained with the velocity calculator 80, the color converter 86 gives red if it is in the first and second quadrants (i.e., $0°<\phi<180°$). This signifies that the Doppler frequency shift is positive, and therefore the blood flows toward the transducer 60. If the phase is in the third and fourth quadrants (i.e., $-180°<\phi<0°$), the color converter gives blue. This signifies that the Doppler frequency shift is negative, and the blood flows away from the transducer 60. The faster the blood flow, the brighter the color becomes.

Secondly, with regard to the variance, the larger its value, the greater the green blend ratio. Since variance represents the flow turbulence, the color hue changes according to its extent; that is, the red approaches yellow, and blue approaches cyan. On the other hand, B-mode image, M-mode image and FFT-analyzed blood-flow data are all converted to black/white as in the conventional way.

The output from the color converter 86 is transformed to analog signals by a D/A converter 88 and is displayed on a color TV screen 90 in real time. Further, the analog signals may be provided to an encoder 92 wherein its output is stored on a video tape recorder 94.

Figure 3:
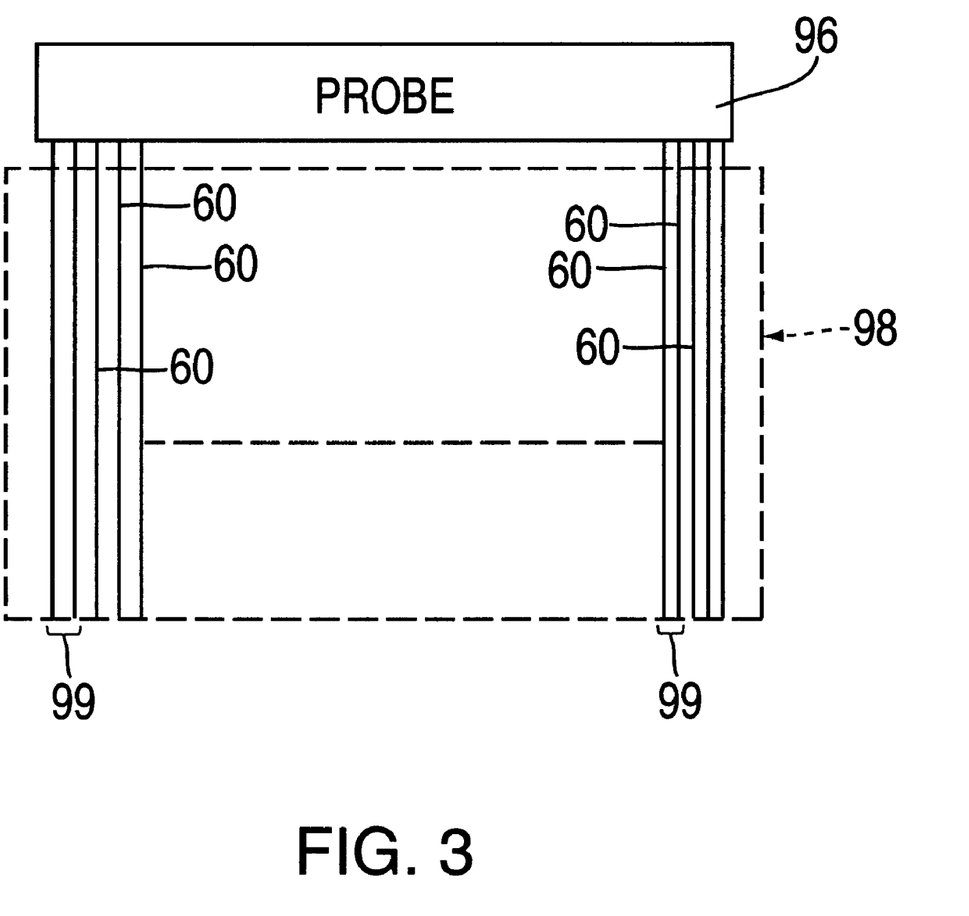
FIG. 3 shows a schematic representation of the imaging field of the present invention.

FIG. 3 illustrates a linear probe 96 that emits and receives a plurality of the scan lines or ultrasound beams 60 through an area of the subject defined as the imaging field 98. While a linear probe 96 is illustrated, one will appreciate that the present invention may be used with any type of probe, such as a phase array, linear probe and curvilinear/convex probe. In accordance with the present invention, the number of transmitted ultrasound beams 60 for scanning a color flow image is approximately 250 beams, each of which are laterally-spaced within the imaging field 98. Each beam 60 is spaced by a predetermined time interval or pulse repetition time (PRT) 99. Contrary to the prior art method of scanning for color flow imaging, the scanning of the imaging field 98 of the present invention is similar to that of scanning a B-mode image in that each of the ultrasound beams 60 are laterally spaced along the imaging field.

Figure 4:
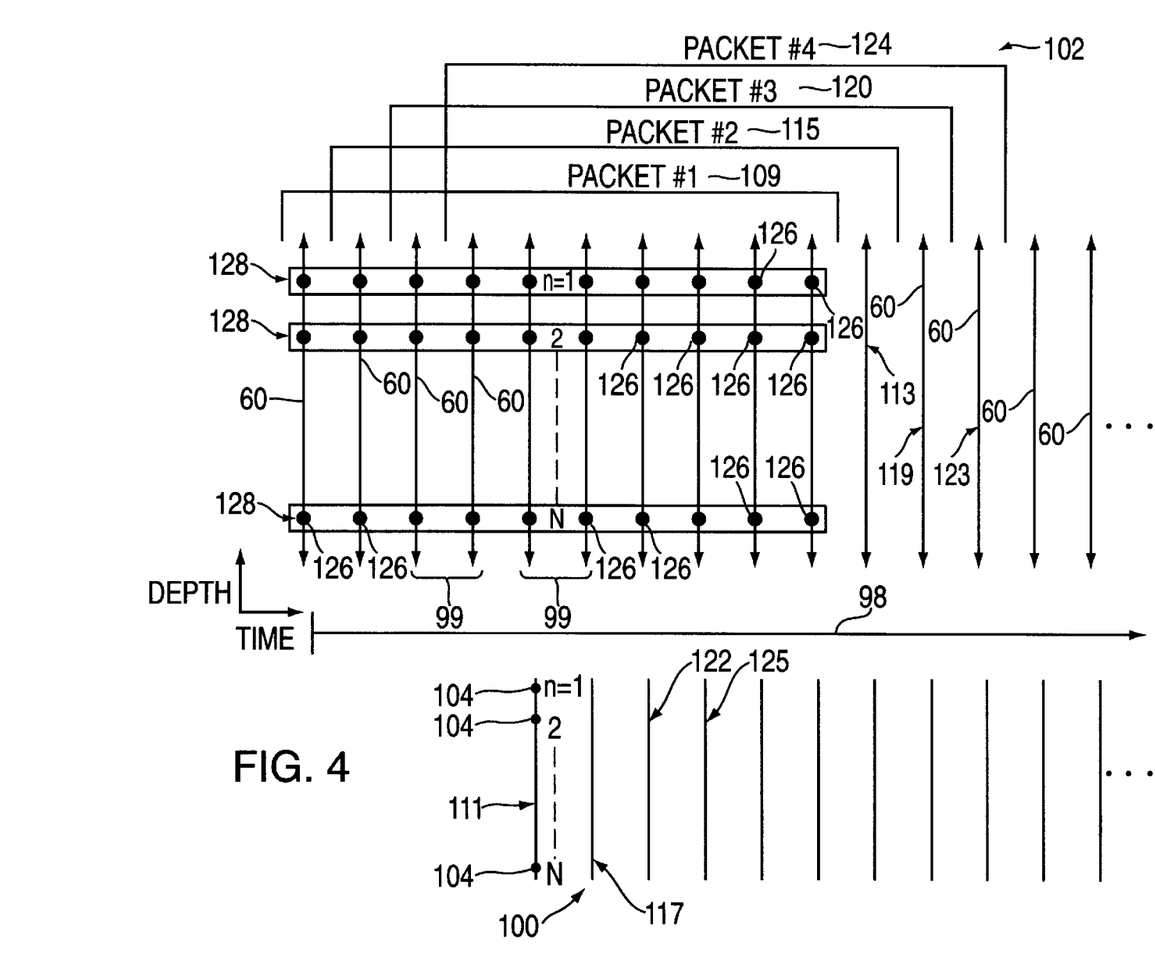
FIG. 4 is a graphical representation of a color flow scanning method embodying the present invention.

FIG. 4 diagrammatically illustrates a representative portion of a number of ultrasound beams 60 scanned through a portion of the imaging field 98 and corresponding calculated color flow output lines 100. The horizontal axis is representative of the scan direction of the ultrasound beams and the vertical axis is representative of the depth or range of the imaging field 98. As described hereinbefore, the method of the present invention for scanning the color flow image is similar to the method of scamming a B-mode image. The ultrasound scan sequence of each transmitted and received (or scanned) ultrasound beam 60 is laterally spaced through the imaging field 98 at a pulse repetition time (PRT) 99. The ultrasound beams 60 are, therefore, transmitted and received only once at each position along the horizontal scanning axis of the imaging field 98. The present method is contrary to the prior art technique, which repeatedly scans a packet 18 of ultrasound beams 12 in the same position in the imaging field as described hereinbefore in FIG. 1. The scanning technique of the present invention is described in the context of a Doppler technique. However, for those skilled in the art, it's apparent that the scanning technique can be used for the time-shift technique with a similar high speed calculator (or processor).

Similar to that of the prior art, the present processing method groups a plurality of ultrasound beams 60 to form packets 102, as shown in FIG. 4, which are used to calculate a respective color flow output line 100 of flow velocities 104 for generating the color flow image. However, the ultrasound beams 60 of each packet 102 in the present invention are laterally spaced or shifted along the horizontal axis rather than disposed in the same position, as shown in FIG. 1.

Figure 5:
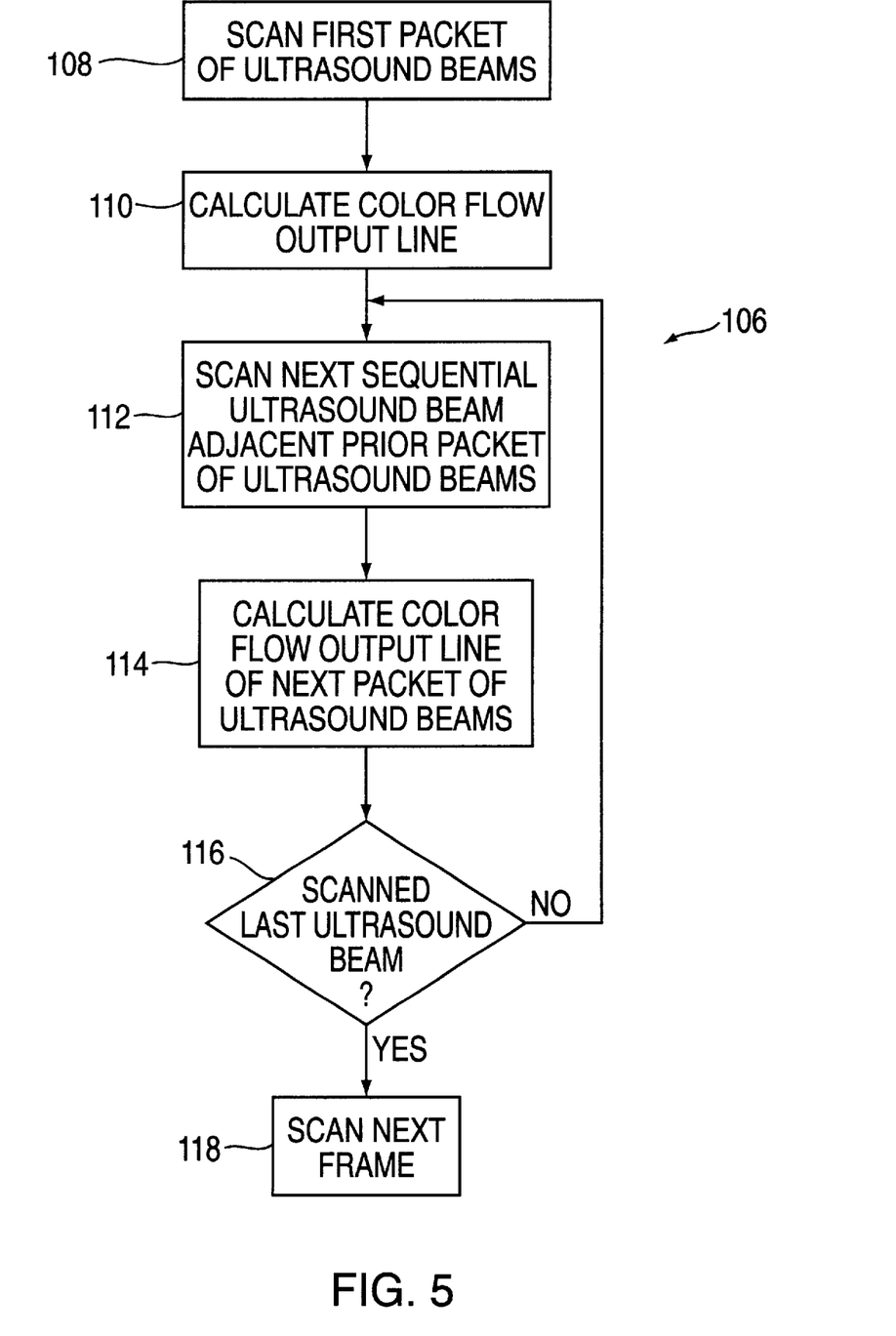
FIG. 5 is a flow diagram of a method of processing a plurality of scanned color flow beams to calculate color flow output lines.

Referring to FIGS. 4 and 5, the processing method 106 comprises in block 108 sequentially scanning from left to right a first packet 109 of a predetermined number of laterally-spaced ultrasound beams 60. For illustrative purposes, each packet 102 of beams 60 is formed of ten (10) beams, however one skilled in the art will appreciate that a packet of ultrasound beams may be defined by any number of beams. In block 110, the first packet 109 of ultrasound beams 60 are then processed to calculate a respective color flow output line 111. In block 112, the imaging system 40 scans the next sequential ultrasound beam 113 to the right of the first packet 109 of beams 60. The last ten (10) scanned beams represent a second packet 115 of ultrasound beams. In block 114, the second packet 115 of ultrasound beams 60 are then processed to calculate a respective color flow output line 117. As shown in block 116, the imaging system 40 repeats steps 112 and 114 to continue to calculate respective color flow output lines for each subsequent packet in the imaging field 98. For example, after the second packet 115 of ultrasound beams 60 have been processed, the imaging system 40 scans the next sequential ultrasound beam 119 to the right of the second packet 115 of beams. The last ten (10) scanned beams represent a third packet 120 of beams. The third packet 120 of beams 60 are then processed to calculate the next respective color flow output line 122.

After the third packet 120 of ultrasound beams 60 have been processed, the imaging system 40 scans the next sequential ultrasound beam 123 to the right of the third packet 120 of beams. The last ten (10) scanned beams 60 represent a fourth packet 124 of beams. The fourth packet 124 of beams 60 are then processed to calculate the next respective color flow output line 125. After one frame of the imaging field 98 has been scanned completely, the imaging system 40 will repeat the sequential scanning of the imaging field for the next frame at block 118.

As best shown in FIG. 4, each received ultrasound beam 60 is represented by N number (typically N=256) of complex Doppler signals 126 depicted by solid circles. Each of the complex signals 126 of the ultrasound beam 60 is representative of the received beam at a defined depth or range in the body or subject. Specifically, the complex signals 126 where n=1 represents the ultrasound signal of the body at a shallower depth (closest to the probe) than the complex signals where n=N represents the image of the body at a deeper depth in the body (furthest from the probe).

In the processing of the each packet 102 of ultrasound beams 60 to calculate a corresponding color flow output line 100, each complex signal 126 of each ultrasound beam of each packet at each depth is used to calculate a resulting flow velocity 104 at a corresponding depth of the color flow output line 100. For example, each of the complex Doppler signals 126 at n=1 of each of the ultrasound beams of the first packet 109 defines a subpacket 128, which is used to calculate the flow velocity 104 at n=1 of the color flow output line 111. Each subpacket of complex signals 126 at each depth (n=2 to N) is sequentially processed to determine the flow velocity 104 at each depth for the color flow output line 100. Specifically, subpacket 128 of complex signals 126 at depth at n=2 is sequentially processed to determine the flow velocity 104 at depth at n=2 of the color flow output line 111.

It is important to note that for each scanned ultrasound beam 60 scanned along the imaging field 98, a resulting color flow output line 100 is generated and therefore, the output line density of the color flow output lines is comparable to the scan density of the ultrasound beam for imaging in the B-mode.

Consequently, the number of calculations required to process the increased number of packets 102 of ultrasound beams 60 increases by several times (6–16 times). The increased number of calculations depends on the packet size as compared to the simple technique of the prior art. The time to process the increased number of packets 102 of ultrasound beams 60 using the prior art color Doppler techniques would, therefore, increase by a factor of 6–16 times.

To overcome this increased processing time, another aspect of the present invention includes a high speed method of calculating and processing the subpackets 128 of complex Doppler signals 126 provided by the scanning method 106 described hereinbefore. Similar to the prior art of color Doppler techniques, the present invention processes the complex signals 126 of each subpacket 128 using an autocorrelation method which uses averaging of autocorrelation in the subpacket in order to increase the signal to noise ratio. As described hereinbefore, received ultrasound signals are high-pass filtered to remove stationary noise (clutter) from tissues after quadrature detected and an autocorrelation (i.e. complex product) between two (2) complex signals are calculated and averaged over the subpacket. This autocorrelation method is expressed mathematically as follows.

$$C_{m,n} = \sum_{i=m+2}^{m+k} z_{i,n} \cdot z^*_{i-1,n} \quad (1)$$

where $C_{m,n}$ is the autocorrelation of a subpacket 128 of complex Doppler signals 126 at a position (m,n); m is the number of the color flow output lines; n is the depth index of the complex signals 126 of an ultrasound beam 60; $z_{i,n}$ is a complex Doppler signal at a position (i,n) after clutter removal (wall filter); $z^*_{i-1,n}$ is complex conjugate of $z_{i-1,n}$; k is a packet size of complex signals after wall filtering; and "•" indicates complex multiplication.

Because each packet 18 of ultrasound beams 12 of FIG. 1 are scanned at the same position and therefore no beams are common between packets, this prior art technique requires that autocorrelation of each subpacket 128 of complex signals 126 be separately calculated using equation (1). In the present invention, however, a substantial number of ultrasound beams 60 of adjacent packets 102 are common which permits the autocorrelation of the prior subpacket 128 of complex signals 126 at the prior position to be used to greatly reduce the number of calculations required to determine the autocorrelation of the subpacket 128 of complex signals 126 at the next lateral position. The autocorrelation of each subpacket of complex Doppler signals in the present invention is therefore expressed by the following equations:

$$C_{m,n} = C_{m-1,n} + [z_{m+k,n} \cdot z^*_{m+k-1,n}] - [z_{m+1,n} \cdot z^*_{m,n}] \quad (2)$$

$$\text{where } C_{m-1,n} = \sum_{i=m+1}^{m+k-1} z_{i,n} \cdot z^*_{i-1,n} \quad (3)$$

In other words, the autocorrelation of the subpacket 128 of the present complex signals can be efficiently calculated using the autocorrelation result of the prior subpacket of complex signals. Specifically, the autocorrelation of the present subpacket of complex signals ($C_{m,n}$) is the autocorrelation of the previous subpacket of signals ($C_{m-1,n}$) and the complex product ($z_{m+k,n} \cdot z^*_{m+k-1,n}$) of the complex signal of the most recently scanned ultrasound beam added to the present subpacket of signals minus the complex product of the last beam of the previous subpacket of signals ($z_{m+1,n} \cdot z^*_{m,n}$).

Figure 6A:
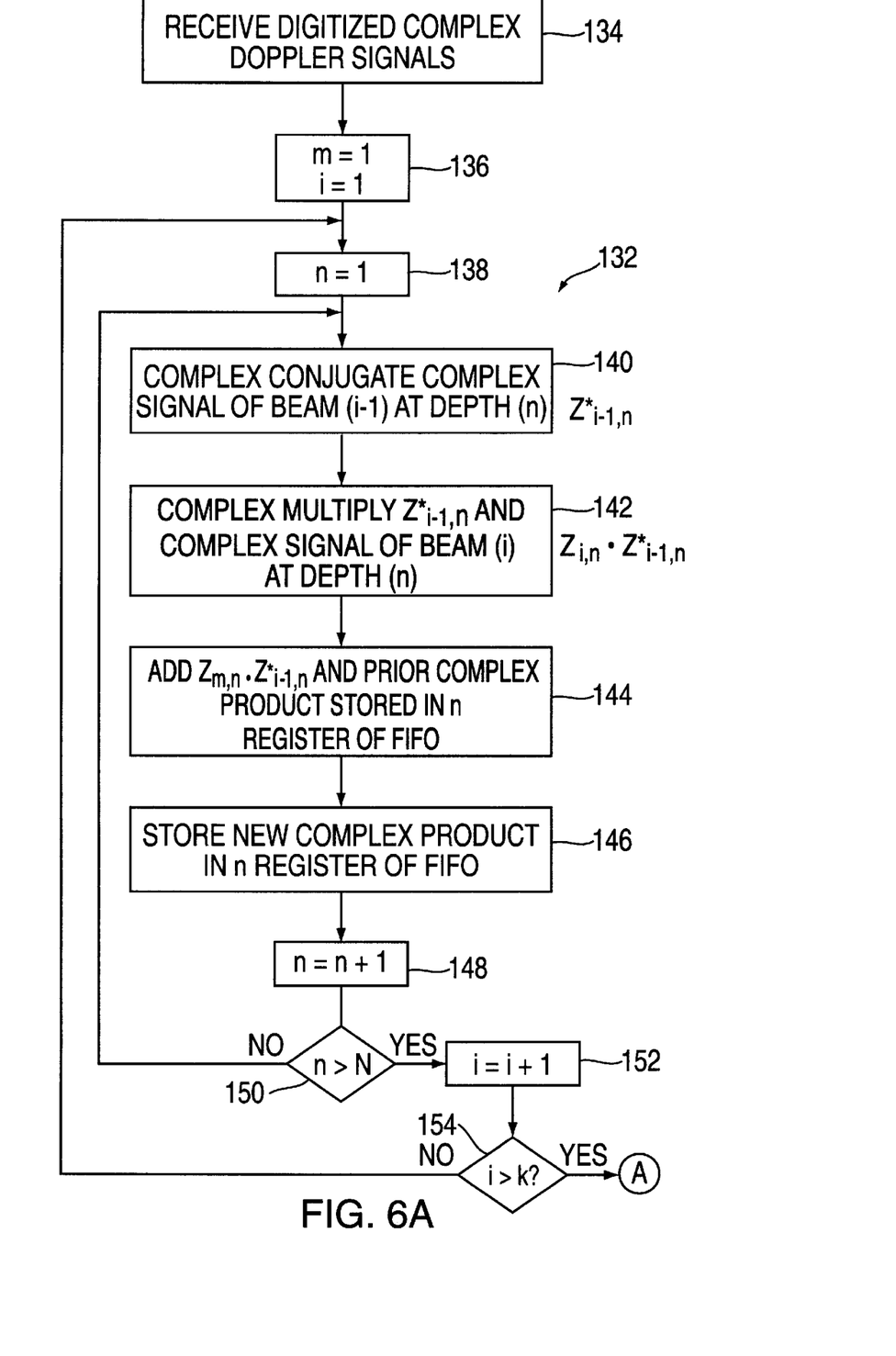
FIGS. 6A and 6B are a flow diagram of a method of high-speed autocorrelation of complex signals representative of the color flow beams.
Figure 6B:
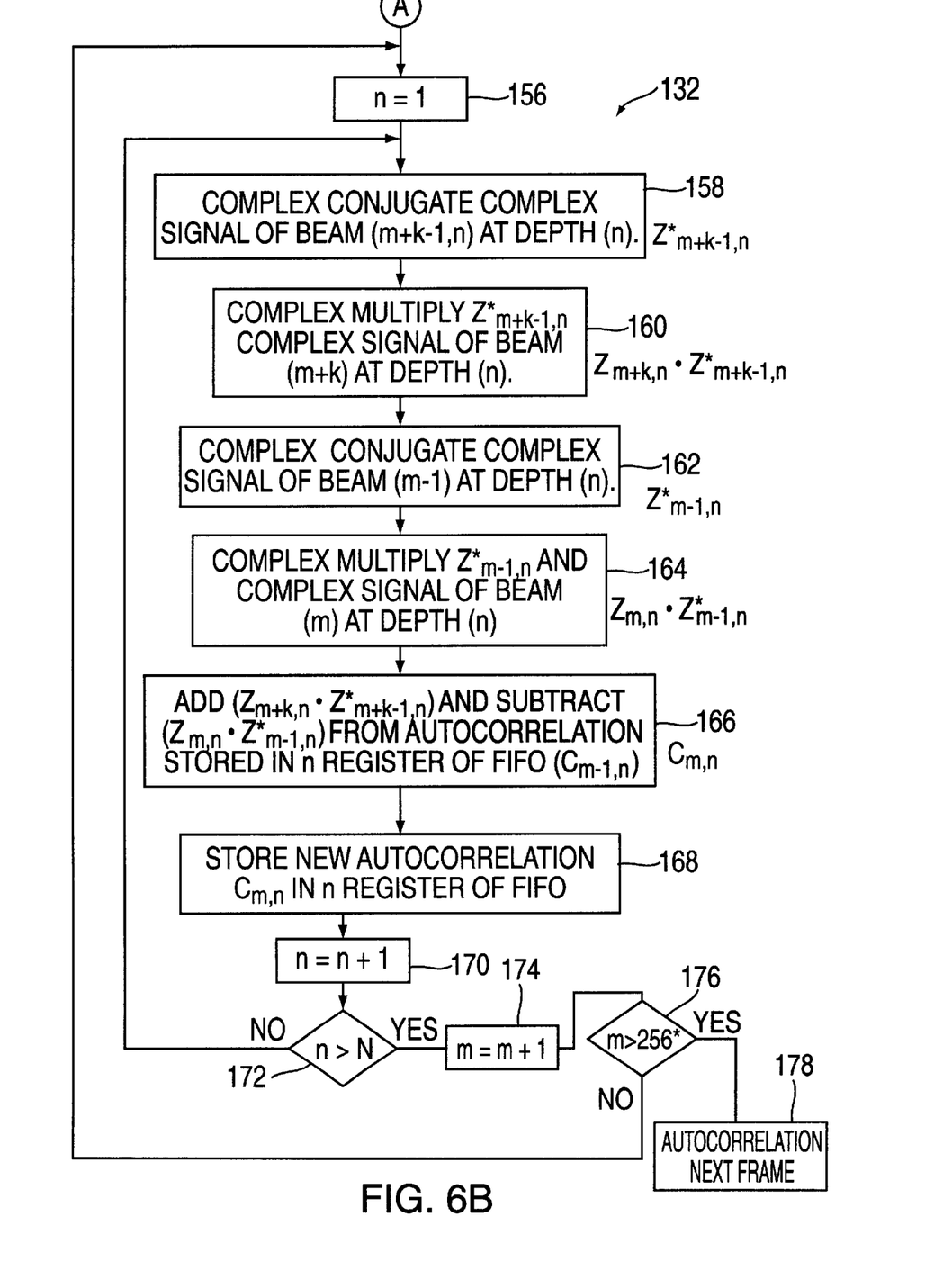

FIGS. 6A and 6B are illustrative of this method 132 of high-speed autocorrelation of complex Doppler signals representative of the ultrasound beams 60. This high-speed autocorrelation can be implemented in an electronic circuit shown in FIG. 7 which should be referenced in order to describe the invention in conjunction with FIG. 6A and FIG. 6B. FIG. 6A depicts the initialization process of the high speed autocorrelation during the processing of the first k beams of a frame. In blocks 134, 136, 138, a first digitized complex Doppler signal ($z_{i,n}$) representative of the depth of the received ultrasound beam closest to the probe is received and stored in memory, preferably a line buffer or first in—first out (FIFO). The complex Doppler signal 126 of the prior beam (i-1) at the same depth at n=1 ($z_{i-1,n}$) is complex conjugated in block 140. In block 142, the complex conjugate signal ($z^*_{i-1,n}$) is complex multiplied with the complex Doppler signal ($z_{i,n}$) of the ultrasound beam (i) at the same depth at n=1. In block 144, the complex product ($z_{i,n} \cdot z^*_{i-1,n}$) is added to the prior sum of complex product of the complex Doppler signals at the depth n=1 stored in an output FIFO. In block 146, the newly calculated sum of complex product is stored in the output FIFO. In other words, during this initialization process, (k-1) number of the complex products ($z_{i,n} \cdot z^*_{i-1,n}$) are summed up by using an output N-words FIFO, the complex multiplier and the N-word input FIFO, as will be described in greater detail hereinafter. Each of these summations of each depth (n) is defined as the autocorrelation of k beams (or first packet of beams). Each autocorrelation at each depth (n) is stored in a register of the output N-words FIFO.

In blocks 148 and 150, the steps of blocks 140, 142, 144 and 146 are repeated for the remaining complex Doppler signals ($z_{i-1,n+1}$ to $z_{i-1,N}$) of the ultrasound beam 60 (i) represented of the signal of the ultrasound beam at the various depths (n). In blocks 152 and 154 after complex Doppler signal 126 at each depth of the ultrasound beam 60 has been autocorrelated, the complex Doppler signals of the next ultrasound beam at each depth are autocorrelated as described hereinbefore.

After the autocorrelation of the complex Doppler signals 126 of a k number of beams 60 (one packet of beams) was obtained, the complex product of the complex Doppler signals of the new received beam (m+k) and of the complex Doppler signals of the next received beam (m+k-1) is determined. Specifically in FIG. 6B, in blocks 156 and 158, the complex Doppler signal of the prior beam (m+k-1) at the same depth at n=1 ($z_{m+k-1,n}$) is complex conjugated. In block 160, the complex conjugate signal ($z^*_{m+k-1,n}$) is complex multiplied with the complex Doppler signal ($z_{m+k,n}$) of the new received ultrasound beam (m+k) at the same depth at n=1.

In block 162, the complex Doppler signal of the prior beam (m) at the same depth at n=1 ($z_{m,n}$) is complex conjugated. In block 164, the complex conjugate signal ($z^*_{m,n}$) is complex multiplied with the complex Doppler signal ($z_{m+1,n}$) of the ultrasound beam (m+1) at the same depth at n=1.

In block 166, the complex product ($z_{m+k,n} \cdot z^*_{m+k-1,n}$) is added to the prior autocorrelation ($C_{m-1,n}$) of the complex Doppler signals of the last k number of beams at the depth n=1 stored in the output FIFO. In addition, the complex product ($z_{m+1,n} \cdot z^*_{m,n}$) is subtracted from the prior autocorrelation ($C_{m-1,n}$) of the complex Doppler signals of the last k number of beams at the depth n=1 stored in the output FIFO. In block 168, the newly calculated autocorrelation ($C_{m,n}$) is stored in the n register of the output N-words FIFO.

In blocks 170 and 172, the steps of blocks 158, 160, 162, 164, 166 and 168 are repeated for the remaining complex Doppler signals ($z_{m+k-1,n+1}$ to $z_{m+k-1,N}$) of the ultrasound beam (m+k-1) representative of the signal of the ultrasound beam at the various depths (n). In blocks 174 and 176 after complex Doppler signal 12 at each depth of the ultrasound beam 60 has been autocorrelated, the complex Doppler signals of the next ultrasound beam at each depth are autocorrelated as described hereinbefore.

After the autocorrelation of the complex Doppler signals of 256 beams (or number of scan lines of the field), the autocorrelation of the complex Doppler signals of the next frame is determined as shown in block 178.

Figure 7:
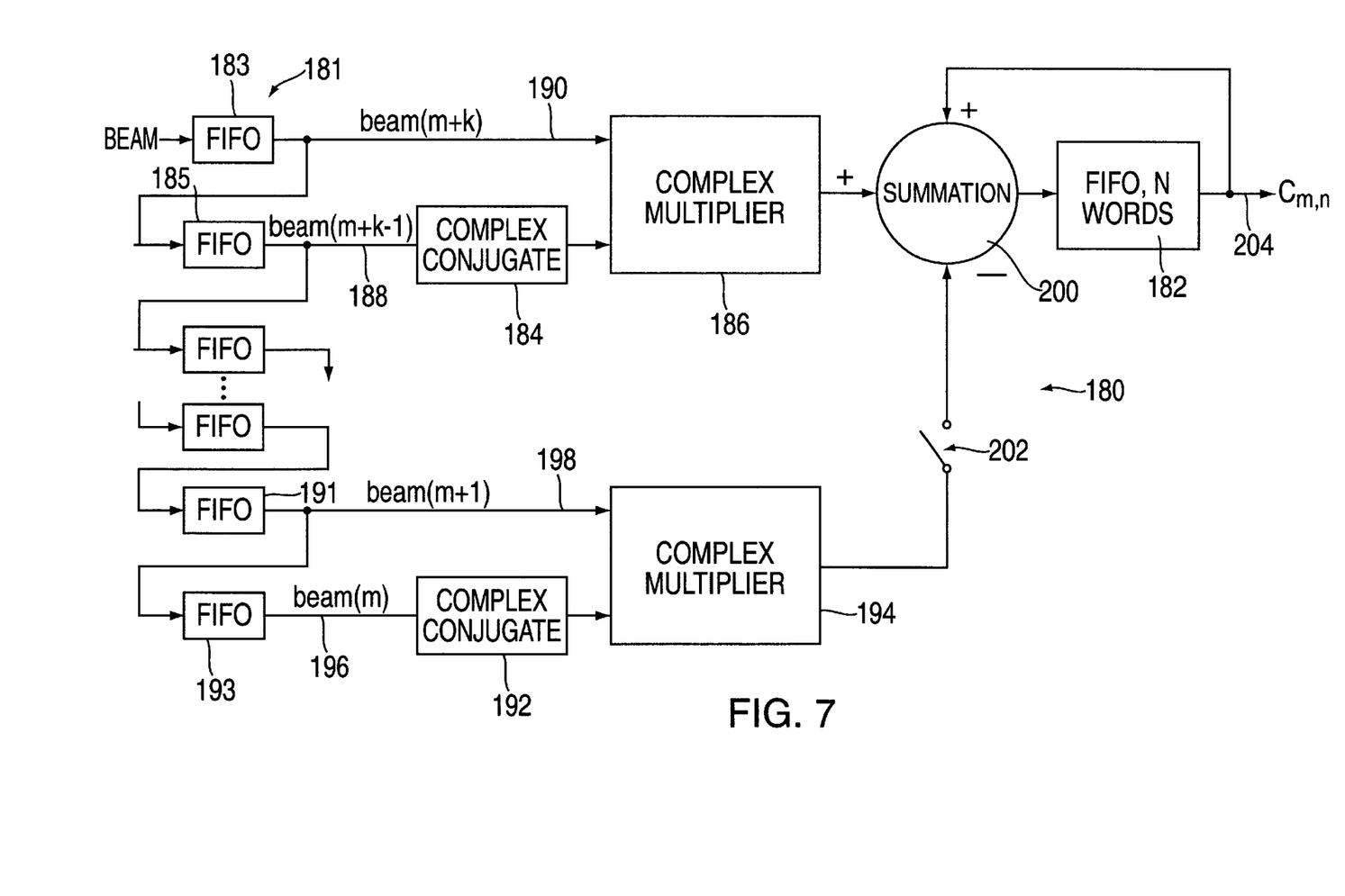
FIG. 7 is a schematic diagram of a circuit for providing high speed autocorrelation calculation for the scanning method of FIG. 4.

This method of high speed autocorrelation may be implemented using an electronic circuit 180 illustrated diagrammatically in FIG. 7. The circuit includes a plurality of input line buffers (or FIFOs) 181 having N number words of storage, which correspond to the number of complex Doppler signals 126 for a single ultrasound beam 60. The circuit includes k+1 number of input FIFOs 181 connected serially to store the complex Doppler signals of a packet of ultrasound beams comprising k number of beams plus the next laterally positioned beam. The circuit sequentially stores each ultrasound beam 60 received by the probe in the first input FIFO 183. The complex signals of each beam is stored in the first FIFO 183 beginning with the complex signal 126 at the nearest depth (at n=1) and sequentially stores the complex signals at each increasing depth from n=2 to n=N. Each input FIFO therefore stores at any given time the complex Doppler signals of the beams of a scanned packet of ultrasound beams. Specifically, the first digitized complex signal at depth n=1 of the first beam is stored in a first storage register of the first FIFO 183. At the next clock cycle, a second digitized complex signal at depth n=2 is stored in the first storage register and the first digitized complex signal is shifted and stored in a second storage register of the first FIFO. After N clock cycles, all the digitized complex signals are stored within the N registers of the first FIFO 183. At the next clock cycle, the first complex signal is provided at the output of the first FIFO 183 and stored in the first register of second FIFO 185. In addition, the first complex signal at depth n=1 of the second beam is stored in the first register of the first FIFO. The above sequence of serially storing the complex signals of the beams continues until k+1 beams are stored in the input FIFOs 181. It is important that the number of registers of the input FIFOs is equal to the number of digitized complex signals representative of an ultrasound beam 60, as will be described in greater detail hereinafter.

The output of the second input FIFO 185 is provided to complex conjugate 184 which calculates the complex conjugate of a complex signal at depth n of beam m+k−1 at input lead 188 to provide the $z^*_{m+k-1,n}$ term of equation (2). The output of the first input FIFO 183 and the output of complex conjugate 184 are provided to complex multiplier 186. The complex multiplier 186 calculates the term $z_{m+k,n} \cdot z^*_{m+k-1,n}$. The complex multiplier 186 multiplies the complex conjugate of the complex Doppler signal at depth n of beam m+k−1 at input lead 188 and the complex value of the complex Doppler signal at depth n of beam $_{m+k}$ at input lead 190 to provide the term $(z_{m+k,n} \cdot z^*_{m+k-1,n})$ of equation (2).

The output of the last input FIFO 193 is provided to complex conjugate 192 which calculates the complex conjugate of a complex signal at depth n of beam m at input lead 196 to provide the $z^*_{m,n}$ term of equation (2). The output of the next to last input FIFO 191 and the output of complex conjugate 192 are provided to complex multiplier 194. The complex multiplier 194 calculates the term $z_{m+1,n} \cdot z^*_{m,n}$. The complex multiplier 194 multiplies the complex conjugate of the complex Doppler signal at depth n of beam $_m$ at input lead 196 and the complex value of the complex Doppler signal at depth n of beam $_{m+1}$ at input lead 198 to provide the term $(z_{m+1,n} \cdot z^*_{m,n})$ of equation (2).

To provide the autocorrelation $C_{m,n}$ of the complex value of the complex signals at depth n of the packet of ultrasound beams, output of complex multiplier 186 and output of output line buffer (FIFO) 182 are summed together and the negative of the output of complex multiplier 194 is summed at 200 when switch 202 is closed. The output value of the summation 200 is then provided to the output FIFO 182 to store the value for the calculation of the autocorrelation of the next subpacket 128 of complex Doppler signals 126 at a depth n. The output FIFO stores the autocorrelation values of the complex Doppler signals at depth n. The output FIFO has N number of words of storage to store the autocorrelation of the complex Doppler signals at each depth n, so that the output value of the output FIFO 182, which is representative of the autocorrelation at a predetermined depth no corresponds to the new autocorrelation when summed in summation 200.

The storage and use of the autocorrelation $C_{m-1,n}$ of a prior packet to calculate the next autocorrelation at a given depth (n) enables minimal calculations to determine the autocorrelation of the complex signals of each successive packet of beams. Unlike the prior art, which requires the complex signals of all the beams of a packet to determine each color flow line 14 (See FIG. 1), the present invention uses the autocorrelation $C_{m-1,n}$ of a prior packet and sums two complex products to provide high-speed calculation of a color flow line.

Another important aspect of the present invention is that each input FIFO 181 and the output FIFO 182 have N words of storage, such that the number of registers of the FIFOs 181, 182 correspond to the number of complex signals comprising an ultrasound beam 60. This shifting of the data in the N-word FIFOs 181, 182 enables increased processing speed to determine the autocorrelation by synchronizing the timing of processing a set of corresponding input complex signals with the corresponding prior autocorrelation in hardware.

Switch 202 is actuated to open a set of contacts at the start of the transmitting of ultrasound beams 60 in the imaging field 98. The switch 202 remains open until k+1 beams are initially acquired and autocorrelated at the beginning of the color flow process, at which time the switch is closed. This operation is representative of the flow diagram illustrated in FIG. 6A.

As illustrated in FIG. 7, the autocorrelation $C_{m,n}$ at output lead 204 is efficiently calculated by calculating two (2) complex conjugates 184, 192; two (2) complex multiplications 186, 194; and three (3) additions 200. If the prior art technique were used, it would require (k−1) complex conjugates, (k−1) complex multiplications, and (k−1) additions.

While a method of processing the ultrasound beams by autocorrelating a plurality of beams for a Doppler technique is described, one skilled in the art will appreciate that a high speed signal processing unit (averaging) can be designed similar to that shown in FIG. 7.

Figure 8:
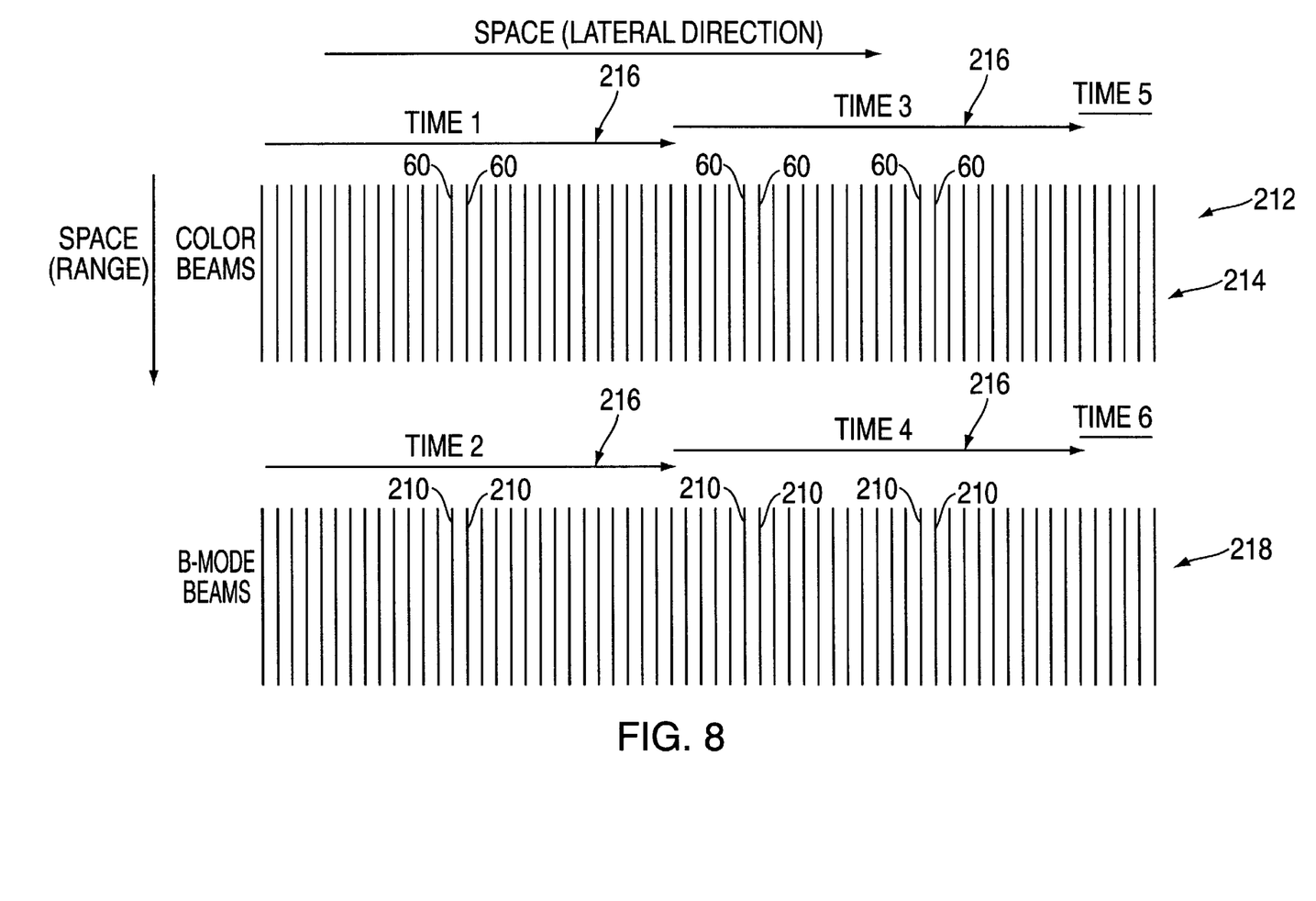
FIG. 8 is a graphical representation of a method of B-mode and color flow scanning embodying the present invention.

The scanning technique of this invention can acquire many more color flow output lines 100 than the prior art. As best shown in FIG. 8, the number of color flow output lines 100 in fact could reach almost that of B-mode beams. We now consider a scanning sequence of color flow and B-mode beams. One method of scamming color flow beams 60 and B-mode beams 210 is to scan the color flow beams 60 from one edge of the frame to the other edge and then scan the B-mode beams from one edge of the frame to the other edge. The B-mode image frame and the color flow image frame are then superimposed on each other. The disadvantage of this technique is the difference in time between the color flow image and the B-mode image that may result in unsynchronized images of B-mode and color flow. This can occur especially in cardiac applications. For example, B-mode image of the left ventricle and blood flow in the left ventricle may not match well using this scanning technique.

FIG. 8 illustrates a scanning technique, which divides a whole scan area into several areas 216. In each area 216, the technique scans (transmit/receive) color flow beams 60 from one edge to an other edge, and then scans B-mode beams 210 in the same area and shifts to the next area. FIG. 8 shows only a portion of the whole frame or imaging field. The upper panel 214 illustrates the scanning of color flow beams 60 and the lower panel 218 illustrates the scanning of B-mode beams 210. First, the color flow scanning in the upper panel 214 starts from the far left side and temporally ends after Time Period 1. Second, B-mode scan starts from the far left side of the lower panel and temporally ends after Time Period 2, covering the same area as color flow during Time Period 1. Third, color flow scanning resumes after Time Period 2 from the point where scanning ended at Time Period 1 and again temporally ends after Time Period 3. B-mode then resumes scanning after Time Period 3 from the point where scanning ended at Time Period 2 and ends after Time Period 4. This process continues until all areas are scanned for color flow and B-mode. The scanning technique alternately scans small areas so that time differences between color flow and B-mode are small and thus the two images are better synchronized. One skilled in the art will appreciate that the Time Periods may be of any suitable length of time to provide sufficient synchronization between the color flow image and B-mode image.

Furthermore, B-mode images can be created from ultrasound signals, acquired for color flow. The prior art of FIG. 1 creates much fewer color flow output lines 14 than B-mode and thus could not yield a high line density for color flow. Therefore, it is not practical to use color flow beams (input) for B-mode imaging. However, the scanning technique of this invention creates a high density of beams 60 for color flow laterally spaced along the imaging field similar to that of the scanning of the B-mode (as shown in FIG. 8), thus color flow beams 60 can be made available for B-mode which needs high resolution. If B-mode images can be created from color flow signals, it increases frame rate and thus is advantageous. In this case, optimization of signal bandwidth can be made between color flow and B-mode.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method for generating color flow images of a subject for an imaging system; said method comprising:
   scanning sequentially a predetermined number of color flow beams through an imaging field wherein the color flow beams are laterally spaced through the imaging field, the color flow beams defining a first packet;
   processing the first packet of color flow beams to generate a first color flow output line;
   scanning an additional color flow beam laterally spaced from a last color flow beam of the first packet, the color flow beams of the first packet and the additional color flow beam, excluding a first color flow beam of the first packet, defining a second packet;
   processing the second packet of color flow beams to generate a second color flow output line; and
   generating a color flow image from the first and second color flow output lines.

2. The method, as defined in claim 1, wherein processing the first packet of color flow beams includes:
   processing a plurality of subpackets of complex signals representative of the color flow beams at a predetermined depth, wherein each subpacket of complex signals comprises a complex signal from each color flow beam of the first packet disposed at the same depth of the subject.

3. The method, as defined in claim 1, wherein processing the second packet of color flow beam signals includes:
   processing a plurality of subpackets of complex signals representative of the color flow beams at a predetermined depth, wherein each subpacket of complex signals comprises a complex signal from each color flow beam of the second packet disposed at the same depth of the subject.

4. The method, as defined in claim 1, wherein processing the first packet of color flow beams includes:
   autocorrelating a plurality of complex signals representative of the color flow beams of the first packet; and
   wherein processing the second packet of color flow beams includes:
   autocorrelating a plurality of complex signals representative of the color flow beams of the second packet.

5. The method, as defined in claim 4, wherein autocorrelating the plurality of complex signals representative of the color flow beams of the second packet is defined by the mathematical expression:

$$C_{m,n} = C_{m-1,n} + [z_{m+k,n} \bullet z^*_{m+k-1,n}] - [z_{m+1,n} \bullet z^*_{m,n}]$$

where $C_{m,n}$ is autocorrelation of the second packet at a position (m,n);
$C_{m-1,n}$ is autocorrelation of the prior (first) packet at a position (m−1,n);
$z_{i,n}$ is a complex signal at a position (i,n);
$z^*_{i-1,n}$ is complex conjugate of $z_{i-1,n}$;
m is the number of the color flow output line;
n is the depth index of the complex signal of the color flow beam;
k is a subpacket size of the complex signals, and
"•" indicates complex multiplication.

6. The method, as defined in claim 1, wherein processing the first packet of color flow beams includes:
   autocorrelating a plurality of complex signals representative of the color flow beams of the first packet disposed at a predetermined depth, defining a prior autocorrelation.

7. The method, as defined in claim 6, wherein processing the second packet of color flow beams includes:
   determining a first complex product of a first complex signal of the last color flow beam of the first packet and a second complex signal of the additional color flow beam at the predetermined depth;
   determining a second complex product of a third complex signal of the first color flow beam of the first packet and a fourth complex signal of a color flow beam scanned after the first color flow beam of the first packet at the predetermined depth; and
   summing the prior autocorrelation, the first complex product and negative of the second complex product to determine a complex signal representative of the second color flow output signal at the predetermined depth.

8. The method, as defined in claim 7, wherein determining the first complex product includes:
   complex conjugating the first complex signal; and
   complex multiplying the second complex signal and the complex conjugate of the first complex signal.

9. The method, as defined in claim 7, wherein determining the second complex product includes:
   complex conjugating the third complex signal; and
   complex multiplying the fourth complex signal and the complex conjugate of the third complex signal.

10. The method, as defined in claim 7, wherein the prior autocorrelation of the first packet is stored in memory.

11. The method, as defined in claim 7, wherein the negative second complex product is summed to the autocorrelation and the first complex product after a predetermined number of color flow beams have been scanned.

12. The method, as defined in claim 7, wherein processing the first packet of color flow beams includes:
   autocorrelating a plurality of complex signals representative of the color flow beams of the first packet disposed at each predetermined depth, defining a plurality of prior autocorrelations.

13. The method, as defined in claim 12, wherein processing the second packet of color flow beams further includes:
   determining a first complex product of a first complex signal of the last color flow beam of the first packet and a second complex signal of the additional color flow beam at each predetermined depth;
   determining a second complex product of a third complex signal of the first color flow beam of the first packet and a fourth complex signal of a color flow beam scanned after the first color flow beam of the first packet at each predetermined depth; and
   summing each respective prior autocorrelation, first complex product and negative of the second complex product to determine a respective complex signal representative of the second color flow output signal at the each predetermined depth.

14. The method, as defined in claim 1, wherein the color flow beams are scanned by a scanning device including at least one of a phased array transducer, a linear transducer and a curvilinear transducer.

15. The method, as defined in claim 1, further comprising:
   processing the color flow beams to generate B-mode output signals; and
   generating a B-mode image from the B-mode output signals.

16. An imaging system for generating color flow images; the imaging system comprising:
   a scanning device configured to scan a plurality of color flow beams through an imaging field, each color flow beam being laterally-spaced through the imaging field; and
   a processor arranged to receive the plurality of color flow beams, the plurality of color flow beams including a predetermined number of the color flow beams defining a first packet, the plurality of color flow beams also including an additional color flow beam defining part of a second packet, the second packet including the additional color flow beam and the color flow beams of the first packet excluding a first color flow beam of the first packet,
   wherein the processor processes the first packet of color flow beams to generate a first color flow output line, processes the second packet of color flow beams to generate a second color flow output line, and generates a color flow image from the first and second color flow output lines.

17. The imaging system, as defined in claim 16, wherein the processor further processes a plurality of subpackets of complex signals representative of the color flow beams at a predetermined depth, wherein each subpacket of complex signals comprises a complex signal from each color flow beam of the first packet disposed at the same depth of the subject.

18. The imaging system, as defined in claim 16, wherein the processor further processes a plurality of subpackets of complex signals representative of the color flow beams at a predetermined depth, wherein each subpacket of complex signals comprises a complex signal from each color flow beam of the second packet disposed at the same depth of the subject.

19. The imaging system, as defined in claim 16, wherein the processor includes an autocorrelator arranged to autocorrelate a plurality of complex signals representative of the color flow beams of the second packet using the autocorrelation result of a plurality of complex signals representative of the color flow beams of the first packet.

20. The imaging system, as defined in claim 19, wherein the autocorrelator is arranged to autocorrelate the plurality of complex signals representative of the color flow beams of the second packet using the mathematical expression:

$$C_{m,n} = C_{m-1,n} + (z_{m+k,n} \bullet z^*_{m+k-1,n}) - (z_{m+1,n} \bullet z^*_{m,n})$$

where $C_{m,n}$ is autocorrelation of the second packet at a position (m,n);
$C_{m-1,n}$ is autocorrelation of the prior (first) packet at a position (m−1,n);
$z_{i,n}$ is a complex signal at a position (i,n);
$z^*_{i-1,n}$ is complex conjugate of $z_{i-1,n}$;
m is the number of the color flow output line;
n is the depth index of the complex signal of the color flow beam;
k is a subpacket size of complex signals, and
"•" indicates complex multiplication.

21. The imaging system, as defined in claim 16, wherein the processor includes an autocorrelator arranged to autocorrelate a plurality of complex signals representative of the color flow beams of the first packet disposed at a predetermined depth, defining a prior autocorrelation.

22. The imaging system, as defined in claim 21, wherein the autocorrelator for processing the second packet of color flow beams is arranged to:
   determine a first complex product of a first complex signal of the last color flow beam of the first packet and a second complex signal of the additional color flow beam at the predetermined depth;
   determine a second complex product of a third complex signal of the first color flow beam of the first packet and a fourth complex signal of a color flow beam scanned after the first color flow beam of the first packet at the predetermined depth; and
   sum the prior autocorrelation, the first complex product and negative of the second complex product to determine a complex signal representative of the second color flow output signal at the predetermined depth.

23. The imaging system, as defined in claim 22, wherein the autocorrelator comprises a summation for summing the prior autocorrelation, the first complex product and negative of the second complex product.

24. The imaging system, as defined in claim 22, wherein the autocorrelator is further arranged to:
   complex conjugate the first complex signal; and
   complex multiply the second complex signal and the complex conjugate of the first complex signal to determine the first complex product.

25. The imaging system, as defined in claim 24, wherein the autocorrelator comprises a complex conjugator for complex conjugating the first complex signal and a complex multiplier for multiplying the second complex signal and complex conjugate of the first complex signal.

26. The imaging system, as defined in claim 22, wherein the autocorrelator is further arranged to:

complex conjugate the third complex signal; and complex multiply the fourth complex signal and the complex conjugate of the third complex signal to determine the second complex product.

27. The imaging system, as defined in claim 26, wherein the autocorrelator comprises a complex conjugator for complex conjugating the third complex signal and a complex multiplier for multiplying the fourth complex signal and complex conjugate of the third complex signal.

28. The imaging system, as defined in claim 22, wherein the autocorrelator includes memory for storing the prior autocorrelation of the plurality of complex signals representative of the color flow beams of the first packet.

29. The imaging system, as defined in claim 22, wherein the negative of the second complex product is summed to the first and second complex products after a predetermined number of color flow beams have been scanned.

30. The imaging system, as defined in claim 22, wherein the autocorrelator further includes a switch for selectively summing the negative of the second complex product to the prior autocorrelation and the first complex product after a predetermined number of color flow beams have been scanned.

31. The imaging system, as defined in claim 16, wherein the processor processes the color flow beams to generate B-mode output signals, and generates a B-mode image from the B-mode output signals.

32. The imaging system, as defined in claim 16, wherein the scanning device includes at least one of a phased array transducer, a linear transducer and a curvilinear transducer.

33. The imaging system, as defined in claim 16, wherein the processor comprises a plurality of input shift registers connected serially for storing a plurality of complex signals representative of the plurality of color flow beams, each shift register comprising a predetermined number of storage registers that equals the number of complex signals representing one color flow beam.

34. The imaging system, as defined in claim 33, wherein the input shift registers are first-in, first-out line buffers.

35. The imaging system, as defined in claim 16, wherein the processor comprises an output shift register for storing a predetermined number of prior autocorrelations, the output shift register comprising a predetermined number of storage registers that equals the number of complex signals representing one color flow beam, said predetermined number of storage registers also being equal to the number of autocorrelations in one color flow output line.

36. The imaging system, as defined in claim 35, wherein the output shift register is a first-in, first-out line buffer.

* * * * *